(12) United States Patent
Reisinger et al.

(10) Patent No.: US 10,327,669 B2
(45) Date of Patent: Jun. 25, 2019

(54) MOUTHPIECE FOR A DEVICE FOR MEASURING A PARAMETER OF RESPIRATORY AIR, AND RESPIRATORY AIR METER

(71) Applicant: Robert Bosch GmbH, Stuttgart (DE)

(72) Inventors: Daniel Reisinger, Rottenburg-Wendelsheim (DE); Klaus Mueller, Stuttgart (DE); Torsten Richter, Darmstadt (DE)

(73) Assignee: Robert Bosch GmbH, Stuttgart (DE)

( * ) Notice: Subject to any disclaimer, the term of this patent is extended or adjusted under 35 U.S.C. 154(b) by 443 days.

(21) Appl. No.: 15/011,945

(22) Filed: Feb. 1, 2016

(65) Prior Publication Data

US 2016/0220148 A1 Aug. 4, 2016

(30) Foreign Application Priority Data

Feb. 3, 2015 (DE) .......... 10 2015 201 826

(51) Int. Cl.
| | |
|---|---|
| *A61B 5/097* | (2006.01) |
| *A63F 13/21* | (2014.01) |
| *A61B 5/08* | (2006.01) |
| *A61B 5/00* | (2006.01) |
| *A61M 15/00* | (2006.01) |

(52) U.S. Cl.
CPC ............ *A61B 5/097* (2013.01); *A61B 5/4845* (2013.01); *A63F 13/21* (2014.09); *A61B 5/08* (2013.01); *A61B 5/682* (2013.01); *A61B 5/7475* (2013.01); *A61M 15/0021* (2014.02)

(58) Field of Classification Search
CPC ......... A61B 5/097; A61B 5/4845; A61B 5/08; A61B 5/682; A61B 5/7475; A63F 13/21; A61M 15/0021
USPC .................................................. 600/529–543
See application file for complete search history.

(56) References Cited

U.S. PATENT DOCUMENTS

| | | | |
|---|---|---|---|
| 4,233,990 A | 11/1980 | Yardley | |
| 5,193,529 A | 3/1993 | Labaere | |
| 5,839,430 A * | 11/1998 | Cama ................... | A61B 5/0871 128/200.14 |
| 7,364,553 B2 * | 4/2008 | Paz ....................... | A61B 5/087 600/529 |
| 7,749,169 B2 * | 7/2010 | Bayer .................... | A61B 5/097 422/84 |
| 7,993,281 B2 * | 8/2011 | Stock .................... | A61B 5/097 600/529 |

(Continued)

FOREIGN PATENT DOCUMENTS

WO    2014/054059 A1    4/2014

*Primary Examiner* — Navin Natnithithadha
(74) *Attorney, Agent, or Firm* — Maginot, Moore & Beck LLP (57) ABSTRACT

A mouthpiece a device for measuring a parameter of respiratory air. The mouthpiece including an end edge of a wall of the mouthpiece, and the end edge is configured to delimit an opening for blowing respiratory air into the mouthpiece. An opening surface of the opening extends transversely with respect to a flow axis of respiratory air blown into the mouthpiece. A contour of the opening forms a D shape or a lens shape, seen in the direction of the flow axis. The opening is delimited by a first opening portion and by a second opening portion adjoining the first opening portion.

18 Claims, 4 Drawing Sheets

(56) References Cited

U.S. PATENT DOCUMENTS

| | | | | |
|---|---|---|---|---|
| 8,109,267 | B2* | 2/2012 | Villax | A61M 15/0045 |
| | | | | 128/203.12 |
| 8,313,440 | B2* | 11/2012 | Friedman | A61B 5/097 |
| | | | | 600/529 |
| 8,910,625 | B2* | 12/2014 | Mullinger | A61M 11/005 |
| | | | | 128/200.16 |
| 2004/0204655 | A1* | 10/2004 | Stock | A61B 5/097 |
| | | | | 600/532 |
| 2004/0260194 | A1* | 12/2004 | Bayer | A61B 5/097 |
| | | | | 600/529 |
| 2005/0137491 | A1* | 6/2005 | Paz | A61B 5/087 |
| | | | | 600/543 |
| 2006/0206034 | A1* | 9/2006 | Stock | A61B 5/097 |
| | | | | 600/532 |
| 2006/0217625 | A1* | 9/2006 | Forrester, Jr. | A61B 5/097 |
| | | | | 600/532 |
| 2009/0013993 | A1* | 1/2009 | Bird | A61M 15/0086 |
| | | | | 128/200.15 |
| 2009/0178676 | A1* | 7/2009 | Villax | A61M 15/0045 |
| | | | | 128/203.15 |
| 2009/0187113 | A1* | 7/2009 | Friedman | A61B 5/097 |
| | | | | 600/543 |
| 2009/0281442 | A1* | 11/2009 | Paz | A61B 5/087 |
| | | | | 600/532 |
| 2010/0147292 | A1* | 6/2010 | Hamaguchi | A61M 11/02 |
| | | | | 128/200.23 |
| 2011/0247617 | A1 | 10/2011 | Nilsson et al. | |
| 2013/0133663 | A1 | 5/2013 | Maksym et al. | |
| 2014/0116426 | A1* | 5/2014 | Mullinger | A61M 11/005 |
| | | | | 128/200.14 |
| 2014/0257127 | A1 | 9/2014 | Smith et al. | |
| 2014/0288454 | A1* | 9/2014 | Paz | A61B 5/4845 |
| | | | | 600/532 |

* cited by examiner

MOUTHPIECE FOR A DEVICE FOR MEASURING A PARAMETER OF RESPIRATORY AIR, AND RESPIRATORY AIR METER

This application claims priority under 35 U.S.C. § 119 to patent application number DE 10 2015 201 826.1, filed on Feb. 3, 2015 in Germany, the disclosure of which is incorporated herein by rereference in its entirety.

BACKGROUND

The present disclosure relates to a mouthpiece for a device for measuring a parameter of respiratory air, and to a respiratory air meter and control appliance for a computer game.

Masks or mouthpieces are used for measurements of pulmonary function or of the gas composition of the respiratory gas. These consumables are needed to ensure that the measuring appliances are not contaminated by microorganisms. Some consumables have further functions. While masks are placed over the mouth and/or nose, the mouthpieces are enclosed by the lips. Mouthpieces presently available on the market have either a round or an oval shape in cross section. Insertion of the mouthpiece too far into the mouth is achieved by a haptic feedback on the lips via circumferential elevations or by ribs.

SUMMARY

Against this background, the approach set out here proposes a mouthpiece for a device for measuring a parameter of respiratory air and a respiratory air meter. Advantageous embodiments are set forth in the description below.

A mouthpiece for a device for measuring a parameter of respiratory air, with a D-shaped or lens-shaped opening cross section of an opening for blowing the respiratory air into the mouthpiece, allows the lips to be easily closed around the mouthpiece, since the here proposed shape of the mouthpiece, at a contact area of the lips with the mouthpiece, corresponds to the shape of the lips in the relaxed state.

According to the proposed concept, problems with closing the lips and with a resulting escape of respiratory air past the mouthpiece and thus past the measuring appliance can be easily avoided. Particularly for the measurement of trace gases, a person using the proposed mouthpiece can be prompted intuitively, by the whistle-like shape, to breathe in a controlled manner and not at the maximum exhalation capacity.

A mouthpiece for a device for measuring a parameter of respiratory air is proposed, wherein an end edge of a wall of the mouthpiece delimits an opening for blowing respiratory air into the mouthpiece, wherein an opening surface of the opening extends transversely with respect to a flow axis of respiratory air to be blown into the mouthpiece, characterized in that a contour of the opening forms a D shape or a lens shape, seen in the direction of the flow axis, and the opening is delimited by a first opening portion and by a second opening portion adjoining the first opening portion.

With the parameter measurement of the respiratory air by means of the device, it is possible, for example, to determine a pulmonary function or the blood alcohol content of a person to be examined. The mouthpiece allows the person to be examined to blow the respiratory air into the device and, for this purpose, it is enclosed by the person as tightly as possible with the lips. The wall can be a closed curved wall of the mouthpiece. Between the end edge forming the opening and a wider end edge located opposite the end edge, the wall can in particular be solid and extend without additional openings. The wall can roughly have a conical shape, of which the narrow end is formed by the opening. The flow axis can represent a flow path along which respiratory air blown through the opening into the mouthpiece passes through the mouthpiece, or a flow path through which air is sucked from the mouthpiece and the opening. From the point of view of a person looking at the mouthpiece, the D shape or lens shape can be understood as the shape of a capital letter D lying on its side or the shape of a lens lying on one of its main sides. The D shape and also the lens shape of the opening contour can be characterized in that a first attachment site, where a first end of the first opening portion and a first end of the second opening portion join each other, forms a discrete first corner point of the opening contour, and a second attachment site, where a second end of the first opening portion and a second end of the second opening portion join, forms a discrete second corner point of the opening contour.

The first corner point and the second corner point can lie opposite each other with mirror symmetry.

According to one embodiment, the wall can have a lip contact area which is to be enclosed by the lips of a person, in order to blow the respiratory air into the opening. The lip contact area can be composed of an upper lip portion, adjoining the first opening portion and to be engaged by an upper lip of the person, and of a lower lip portion, adjoining the second opening portion and to be engaged by a lower lip of the person. The upper lip portion can have a curve about the flow axis. In this configuration, the mouthpiece can be adapted particularly well to a basic shape of the human upper lip.

According to one embodiment, the first opening portion can extend away from the opening in the direction of the flow axis and, seen in the direction of the flow axis, can have an arch shape, in particular wherein a curvature of the arch lessens as the distance from the opening increases. In this way, a low-turbulence flow of air in the mouthpiece is ensured, which allows air to be blown in with very little air resistance, such that the parameters of the respiratory air that are to be measured can be detected very accurately.

According to a further embodiment, the wall can be configured tapering toward the opening from a wider end edge of the wall lying opposite the end edge. This results in a continuously increasing cross section of the mouthpiece, which can allow the user to find the individually optimal position for performing the breathing maneuver.

For example, a shortest straight connecting line from a wider end edge of the wall, lying opposite the end edge of the wall, to an outermost endpoint of the upper lip portion can be longer than a shortest straight connecting line from the wider end edge of the mouthpiece to an outermost endpoint of the lower lip portion. The configuration of the opening with a slightly protruding upper lip portion is able to ensure the most effective introduction of the respiratory air into the mouthpiece.

Moreover, the mouthpiece, on a side lying opposite the opening, can have an outlet nozzle for letting the respiratory air out of the mouthpiece into a device coupled to the mouthpiece. For example, the outlet nozzle can have an oval cross section. Particularly in the configuration with an oval cross section, the outlet nozzle has the advantage of enabling the respiratory air to move without loss, and with optimal flow, from the mouthpiece into the device.

According to one embodiment of the mouthpiece, an opening surface of the outlet nozzle can be larger than the opening surface of the opening for blowing respiratory air into the mouthpiece. It is thereby possible to easily achieve a suitably controlled blowing of respiratory air into the mouthpiece.

Moreover, an opening surface of the outlet nozzle and the opening surface of the opening for blowing respiratory air into the mouthpiece may only partially overlap. With this embodiment, an advantageous flow of the respiratory air through the mouthpiece can be ensured. The circumferential elevation provides an additional haptic feedback to the lips, such that lip contact with the appliance is avoided. This could also be made higher depending on the product design.

It is also expedient if the mouthpiece has a flange portion, arranged between the wall and the connection nozzle, for flange-mounting the mouthpiece onto a device. On the one hand, secure and robust fastening of the mouthpiece to the device can thus be ensured, and, on the other hand, insertion of the mouthpiece too deep into the mouth of a user can be avoided.

According to a particular embodiment of the mouthpiece, the second opening portion of the opening can be configured as a straight line or be rectilinear. In this way too, it is possible to ensure that the introduction of the respiratory air into the mouthpiece is as effective as possible.

In particular, the lower lip portion of the lip contact area can have the shape of a lateral surface portion of a cylinder. This special configuration of the lower lip portion can make it easier for a user to press the lower lip onto the mouthpiece, thereby facilitating the tight closure of the lips around the mouthpiece.

The lower lip portion can have a convex curve as viewed from an interior of the mouthpiece. With this embodiment too, it is possible to obtain the best possible flow path of the respiratory air through the mouthpiece.

According to another particular embodiment, the second opening portion of the opening can have the shape of a wider arch. A mouthpiece configured in this way can be produced cost-effectively and can be used in a particularly versatile way.

A respiratory air meter is proposed, with the following features:
  a device for measuring a parameter of respiratory air; and
  a mouthpiece according to a variant presented here, wherein the mouthpiece is coupled or can be coupled to the device via a respiratory air interface.

In particular, the respiratory air meter can be designed as a control appliance for controlling a game, for example a computer game.

The object of the disclosure can also be achieved quickly and efficiently by means of this embodiment variant of the disclosure in the form of a device. The device can be used in the medical field, for example for the measurement of respiratory gas. In a particular embodiment, the device can also be used for breathing-controlled operation of computers, e.g. for physically disabled persons, or for controlling (computer) games.

BRIEF DESCRIPTION OF THE DRAWINGS

The approach proposed here is explained in more detail below with reference to examples in the attached drawings, in which.

DETAILED DESCRIPTION

In the following description of preferred illustrative embodiments of the present disclosure, elements depicted in the various figures and having a similar action are labeled with the same or similar reference signs, and the description of these elements is not repeated.

Figure 1:
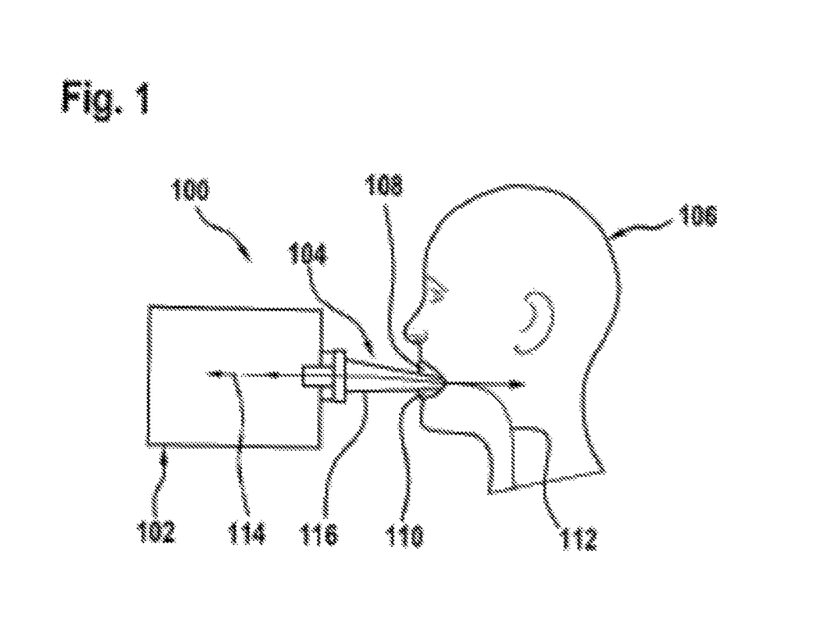
FIG. 1 shows a schematic view of a device for measuring a parameter of respiratory air, according to an illustrative embodiment of the present disclosure.

FIG. 1 shows a schematic view of a respiratory air meter 100 according to an illustrative embodiment of the present disclosure. The respiratory air meter 100 in the depicted illustrative embodiment is an apparatus or a part of an apparatus for performing a pulmonary function test. The respiratory air meter 100 has a device 102 for measuring a parameter of respiratory air, and a mouthpiece 104 coupled to the device 102.

During a use of the respiratory air meter 100, a user 106, here a person to be examined, places in his mouth an end area of the mouthpiece 104 having an opening and closes his lips as tightly as possible around the mouthpiece 104 by pressing the upper lip 108 onto an upper side of the mouthpiece 104 and by pressing the lower lip 110 onto an underside of the mouthpiece 104. When the user 106 then exhales, respiratory air 112 from the user's lungs flows through the mouthpiece 104, along a flow axis 114 of the mouthpiece 104, and into the device 102 coupled to the mouthpiece 104. There, the respiratory air 112 or a pressure of the respiratory air 112 is analyzed.

As is shown in the view in FIG. 1, a wall 116 of the mouthpiece 104 has a tapering configuration, wherein a narrow end of the wall 116 forms a contact area of the mouthpiece 104 to be enclosed by the lips 108, 110. In the illustrative embodiment shown in FIG. 1, the mouthpiece 104 has a lens shape in cross section, as will be discussed in more detail further below.

During a respiratory gas diagnosis performed with the aid of the mouthpiece 104, the entire flow of respiratory air 112 has to be delivered to the meter 100 in order to measure the gas composition of the respiratory air. During the measurement of the pulmonary function and of the main constituents of the respiratory air, breathing is performed with high flow rates; during the measurement of trace constituents, e.g. alcohol or NO, low flow rates of respiratory air 112 are measured.

Figure 2:
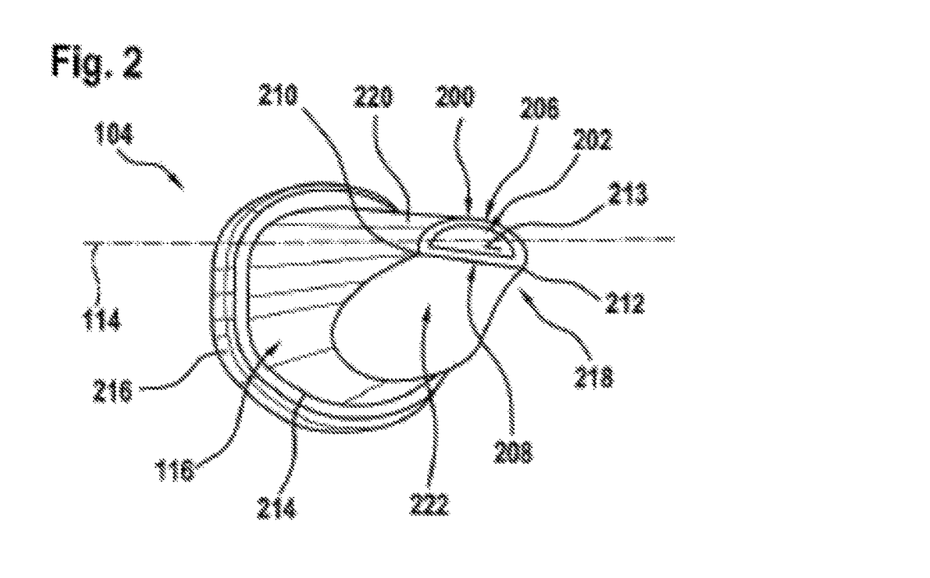
FIGS. 2 to 7 show various views of a mouthpiece for a device for measuring a parameter of respiratory air, according to an illustrative embodiment of the present disclosure.

FIG. 2 is a perspective view showing another illustrative embodiment of the mouthpiece 104 for a device for measuring a parameter of respiratory air. The wall 116 has a roughly conical profile. At a side of the mouthpiece 104 to be directed toward the user, i.e. at the narrow end of the cone, an end edge 200 of the wall 116 forms an opening 202 for blowing respiratory air into the mouthpiece 104.

In the mouthpiece 104 shown by way of an example in FIG. 2, a contour of the opening 202 has the shape of a capital letter D lying on its side. Correspondingly, a first opening portion 206 of the opening 202 has the shape of an arch, and a second opening portion 208 of the opening 202 has the shape of a straight line.

As is shown in the view in FIG. 2, the opening 202 forms two corner points lying opposite each other with mirror symmetry. A first corner point 210 is formed at a first attachment site where a first end of the first opening portion 206 and a first end of the second opening portion 208 join each other. A second corner point 212 is formed at a second attachment site where a second end of the first opening portion 206 and a second end of the second opening portion 208 join each other. An opening surface 213 of the opening 202 extends transversely with respect to the flow axis 114 of the exhaled air and inhaled air through the mouthpiece 104, said flow axis 114 being indicated by a broken line in the figure.

A wider end edge 214 of the wall 116, lying opposite the end edge 200 of the wall 116, has a maximum diameter of the cone-shaped mouthpiece 104. The wider end edge 214 forms a fully circumferential flange 216 for mounting the mouthpiece 104 on a device, for example the respiratory air meter shown in FIG. 1. In some illustrative embodiments, the flange 216 may also have been produced separately and been firmly connected to the wider end edge 214 during the process of manufacture of the mouthpiece 104.

An area of the wall 116 adjoining the opening 202 forms a lip contact area 218 which, during the use of the mouthpiece 104, is enclosed by the user's lips in order to blow respiratory air into the opening 202 or to suck air out of the opening 202. The lip contact area 218 is composed of an upper lip portion 220 adjoining the first opening portion 206, and a lower lip portion 222 adjoining the second opening portion 208.

The upper lip portion 220 curves about the flow axis 114. The lower lip portion 222 closes a cutout from the cone-shaped wall 116 and curves, in the direction of an interior of the mouthpiece 104, between the end edge 200 of the wall 116 with a minimum diameter and a position in the middle area of the wall 116 with a substantially greater but not maximum diameter.

During use, when the mouthpiece 104 is coupled to a device for measuring a parameter of respiratory air, the user closes his lips around the lip contact area 218 in order to blow air into the mouthpiece 104 or to suck air out of the mouthpiece 104, and the user does this by pressing his upper lip onto the upper lip portion 220 and pressing his lower lip onto the lower lip portion 222.

Figure 3:
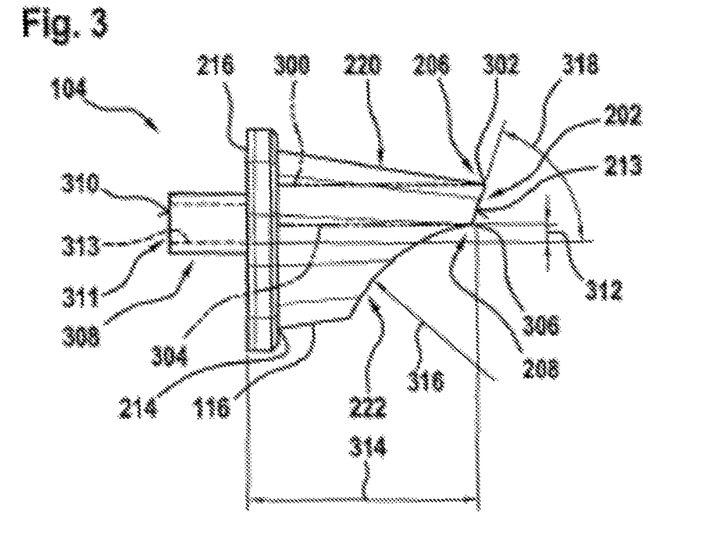

FIG. 3 shows the example of a mouthpiece 104 from FIG. 2 in a side view. It clearly shows the profile of the wall 116 tapering from the wider end edge 214 of the wall 116 toward the opening 202. The side view also shows that the first opening portion 206 of the opening 202 protrudes in relation to the second opening portion 208. Accordingly, a shortest straight connecting line 300 between the wider end edge 214 of the wall 116 and an outermost endpoint 302 of the upper lip portion 220 is greater than a shortest straight connecting line 304 from the wider end edge 214 of the wall 116 of the mouthpiece 104 to an outermost endpoint 306 of the lower lip portion 222.

In the side view of the example of a mouthpiece 104 shown in FIG. 3, the cutout made in the conical wall 116, and forming the lower lip portion 222, has the shape of a lateral surface portion of a cylinder. The lower lip portion 222 begins directly at the second opening portion 208 and ends at a distance from the wider end edge 214 of the wall 116. Seen from an interior of the mouthpiece 104, the lower lip portion 222 in the illustrative embodiment shown in FIG. 3 has a convex curve.

The side view of the example of a mouthpiece 104 in FIG. 3 shows an outlet nozzle 308 for letting exhaled air from the mouthpiece 104 into a device coupled to the mouthpiece 104. The outlet nozzle 308 sits on the flange 216 at a side of the mouthpiece 104 opposite the opening 202 and in this case has the shape of a tube with a constant diameter.

It will be seen from the view in FIG. 3 that an opening surface 310 of an opening 311 of the outlet nozzle 308 and the opening surface 213 of the opening 202 do not completely overlap. In the illustrative embodiment shown, the opening surface 310 of the outlet nozzle 308 lies deeper than the opening surface 213 of the opening 202. To be specific, an offset 312 between an outer edge of the second opening portion 208 and a surface of an inner wall 313 of the outlet nozzle 308 measures 3 millimeters.

As further specific dimensions, a length 314 of the mouthpiece 104 from a main side of the flange 216, facing the outlet nozzle 308, to the endpoint 306 of the second opening portion 208 measures 43 millimeters. A radius 316 of the lower lip portion 222 forming a portion of a cylinder wall measures 30 millimeters, and an angle 318 between the upper lip portion 220 and a continuation of the inner wall 313 of the connection nozzle 308 measures 75 degrees.

Figure 4:
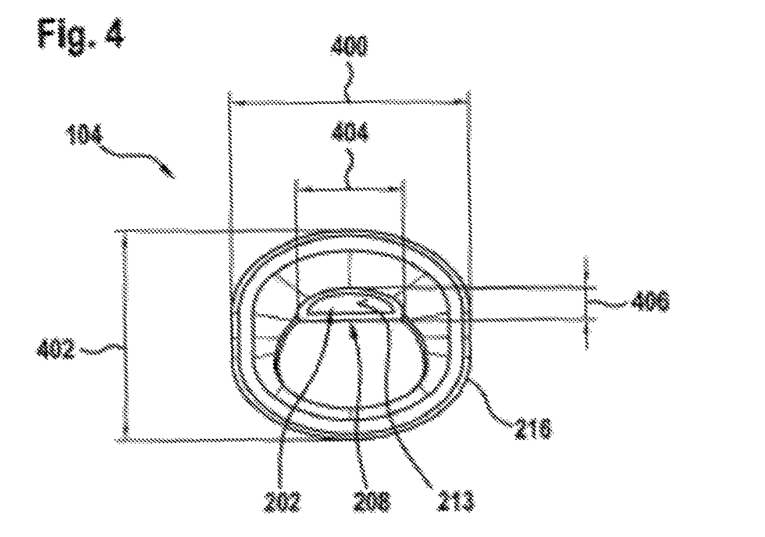

FIG. 4 shows a front view of the example of a mouthpiece 104 from FIG. 2. An overall width 400 of the mouthpiece 140 including the flange 216 measures 47 millimeters in this example of a mouthpiece 104, and an overall height 402 including the flange 216 measures 41 millimeters. A maximum width 404 of the D-shaped opening 202, which corresponds to the length of the straight second opening portion 208 in the illustrative embodiment shown, measures 22 millimeters, and a maximum height 406 of the opening 202 measures 7 millimeters.

The view in FIG. 4 shows clearly how the continuously increasing cross section of the mouthpiece 104 allows the user to find the individually optimal position for performing the breathing maneuver, without air being blown past the appliance.

Figure 5:
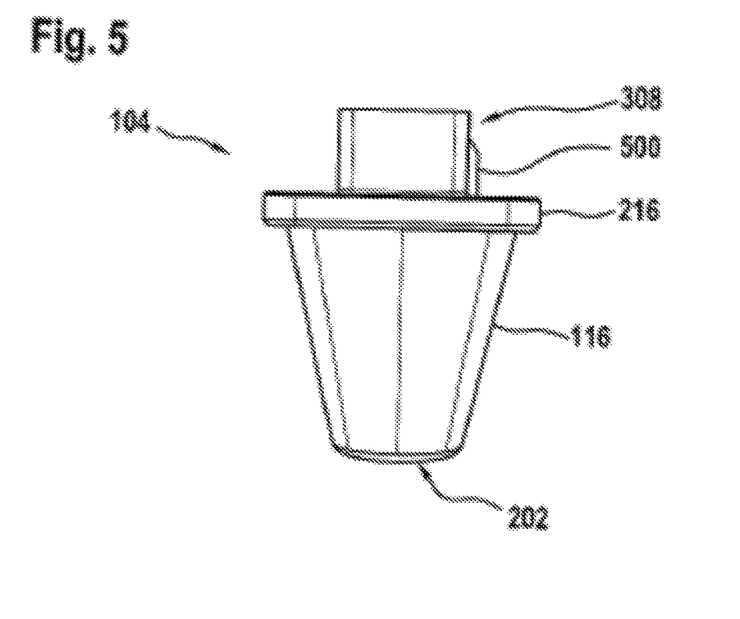

FIG. 5 shows a plan view of the example of a mouthpiece 104 from FIG. 2. Here, the tapering profile of the wall 116 of the mouthpiece 104 from the flange 216 to the opening 202 can once again be clearly seen. It also shows that the wall 116 is solid, i.e. has no openings of any kind, between the flange 216 and the opening 202.

The example of a connection nozzle 308 shown in FIG. 5 is provided laterally with a projection 500. The projection 500 permits a correctly positioned insertion of the mouthpiece 104 into a receiving area of a device which is to be coupled to the mouthpiece 104 and which is used for measuring a parameter of respiratory air and, according to one illustrative embodiment, for securely locking the mouthpiece 104 in the device. Moreover, the projection 500 can serve for detecting a correctly fitted mouthpiece in the measuring device.

Figure 6:
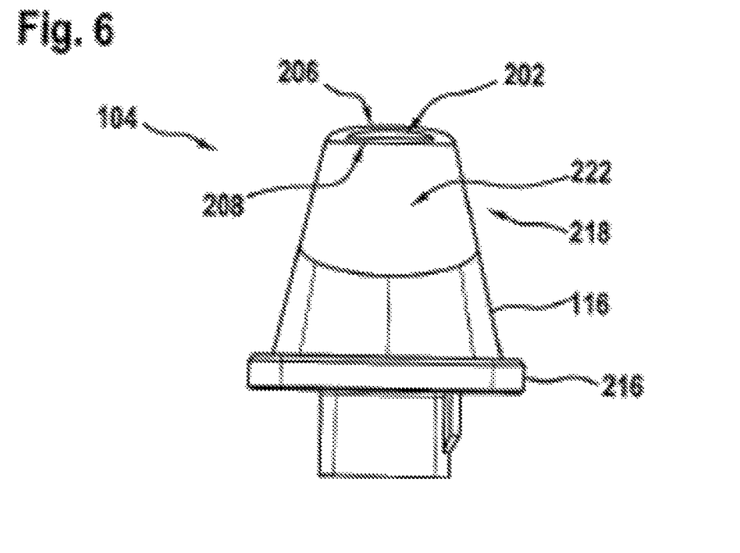

FIG. 6 shows a bottom view of the example of a mouthpiece 104 from FIG. 2. It can be clearly seen here that the lower lip portion 222 of the lip contact area 218 widens gradually from the opening 202 in the direction of the flange 216 and extends over more than half of an underside of the wall 116. Thus, every user of the mouthpiece 104, seeking to close the lips optimally around the lip contact area 218, can comfortably find the suitable position for the lower lip. The view in FIG. 6 also clearly shows how the first opening portion 206 of the opening 202 protrudes in relation to the second opening portion 208.

Figure 7:
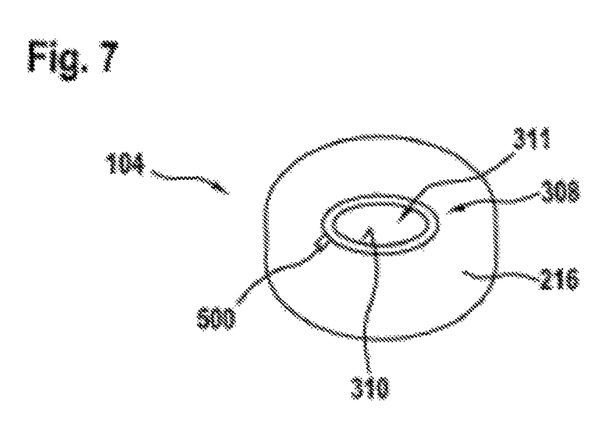

FIG. 7 shows a rear view of the example of a mouthpiece 104 from FIG. 2. It depicts a main face of the flange 216, which is directed away from a user of the mouthpiece 104 during use, and from the approximate center of which the connection nozzle 308 protrudes. In the illustrative embodiment shown in FIG. 7, a contour of the connection nozzle 308 has, in cross section, the shape of a symmetrical, elongate oval lying on its side. Thus, the shape of the connection nozzle 308 partially corresponds to the shape of the opening 202 at the other end of the mouthpiece 104. A comparison of the view in FIG. 7 with the view in FIG. 4 shows that, in the mouthpiece 104 shown as an example, the opening surface 310 of the opening 311 of the outlet nozzle 308 is larger than the opening surface 213 of the opening 202 for blowing respiratory air into the mouthpiece 104.

Figure 8:
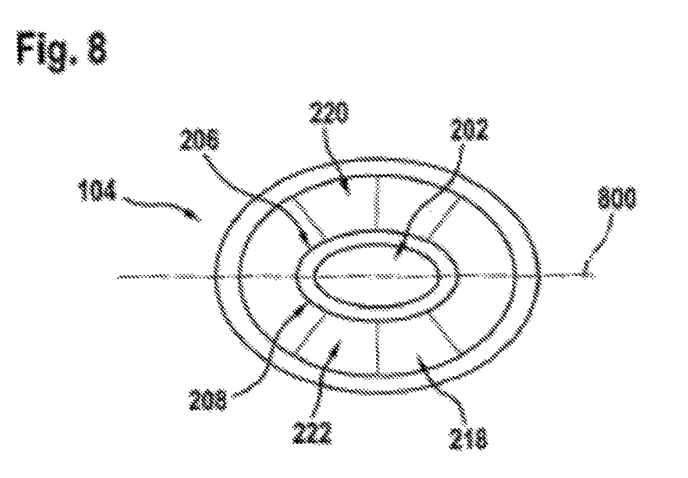
FIG. 8 shows a front view of a mouthpiece for a device for measuring a parameter of respiratory air, according to a further illustrative embodiment of the present disclosure.

FIG. 8 shows a front view of the example of a mouthpiece 104 from FIG. 1. It will be seen from this view that the opening 202 for blowing respiratory air into the mouthpiece 104 has a lens shape. Here, both the first opening portion 206 and also the second opening portion 208 of the opening 202 have the arch shape which, in the illustrative embodiment of the mouthpiece 104 shown in FIGS. 2 to 7, is possessed only by the first opening portion 206. In the illustrative embodiment of the mouthpiece 104 shown in FIG. 8, the upper lip portion 220 and the lower lip portion 222 of the lip contact area 218 have mirror symmetry with respect to an axis of reflection 800.

The illustrative embodiments described, and shown in the figures, are only chosen as examples. Different illustrative embodiments may be combined with one another either completely or in terms of individual features. An illustrative embodiment can also be supplemented by features of another illustrative embodiment.

Moreover, the method steps presented here can be repeated, and they can be carried out in an order different than that described.

If an illustrative embodiment comprises an "and/or" link between a first feature and a second feature, this should be read as meaning that the illustrative embodiment, in one form, has both the first feature and also the second feature and, in another form, has either just the first feature or just the second feature.

What is claimed is:

1. A mouthpiece for a device for measuring a parameter of respiratory air, the mouthpiece comprising:
   a wall including an end edge having a first opening portion and a second opening portion adjoining the first opening portion, wherein:
      the first opening portion and the second opening portion delimit an opening configured for blowing respiratory air into the mouthpiece;
      a contour of the opening forms a D shape or a lens shape, seen in a direction of a flow axis of respiratory air to be blown into the mouthpiece; and
      the first opening portion extends beyond the second opening portion along the flow axis, such that an opening surface of the opening defined by the first opening portion and the second opening portion is at a transverse angle with respect to the flow axis; and
   a side lying opposite the opening; and
   an outlet nozzle on the side, the outlet nozzle configured to let the respiratory air out of the mouthpiece into a device coupled to the mouthpiece, the outlet nozzle having an oval cross section, wherein an opening surface of the outlet nozzle and the opening surface of the opening for blowing respiratory air into the mouthpiece only partially overlap each other.

2. The mouthpiece according to claim 1, wherein:
   the wall has a lip contact area configured to be enclosed by the lips of a person to blow the respiratory air into the opening, and
   the lip contact area includes:
      an upper lip portion, adjoining the first opening portion and configured to be engaged by an upper lip of the person, the upper lip portion having a curve about the flow axis and
      a lower lip portion, adjoining the second opening portion and configured to be engaged by a lower lip of the person.

3. The mouthpiece according to claim 1, wherein:
   the wall includes a wider end edge lying opposite the end edge, and
   a shortest straight connecting line parallel with the flow axis extending from the wider end edge to an outermost endpoint of the upper lip portion is longer than a shortest straight connecting line parallel with the flow axis extending from the wider end edge to an outermost endpoint of the lower lip portion.

4. The mouthpiece according to claim 1, wherein the second opening portion of the opening is configured as a straight line.

5. The mouthpiece according to claim 1, wherein the lower lip portion of the lip contact area is shaped as a lateral surface portion of a cylinder.

6. The mouthpiece according to claim 1, wherein the lower lip portion of the lip contact area has a convex curve as viewed from an interior of the mouthpiece.

7. The mouthpiece according to claim 1, wherein the second opening portion of the opening is shaped as a wider arch.

8. The mouthpiece according to claim 1, wherein, seen in the direction of the flow axis, the first opening portion has an arch shape.

9. The mouthpiece according to claim 8, wherein a curvature of the arch lessens as a distance from the opening increases.

10. The mouthpiece according to claim 1, wherein:
    the wall includes a wider end edge lying opposite the end edge, and
    the wall tapers monotonically toward the opening from the wider end edge.

11. The mouthpiece according to claim 1, wherein an opening surface of the outlet nozzle is larger than the opening surface of the opening for blowing respiratory air into the mouthpiece.

12. The mouthpiece according to claim 1, further comprising:
    a flange portion arranged between the wall and the outlet nozzle, the flange portion configured to flange-mount the mouthpiece onto the device.

13. A respiratory air meter or control appliance for a game, comprising:
    a device configured to measure a parameter of respiratory air; and
    a mouthpiece comprising:
       a wall having an end edge having a first opening portion and a second opening portion adjoining the first opening portion, wherein:
          the first opening portion and the second opening portion delimit an opening configured for blowing respiratory air into the mouthpiece;
          a contour of the opening forms a D shape or a lens shape, seen in a direction of a flow axis of respiratory air to be blown into the mouthpiece; and
          the first opening portion extends beyond the second opening portion along the flow axis, such that an opening surface of the opening defined by the first opening portion and the second opening portion is at a transverse angle with respect to the flow axis, wherein the mouthpiece is configured to be coupled to the device via a respiratory air interface; and an output nozzle positioned at an end of the flow channel opposite the opening so that a central axis of the output nozzle is parallel to but offset from the flow axis, such that an opening surface of the outlet nozzle and the opening for blowing respiratory air into the mouthpiece only partially overlap each other.

14. A mouthpiece for a device for measuring a parameter of respiratory air, comprising:

an upper body portion with a first end edge; and
a lower body portion with a second end edge,
  the upper and lower body portions together defining a flow channel along a flow axis such that the first and second end edges form an opening into the flow channel configured to receive respiratory air,
  the first end edge positioned beyond the second end edge along the flow axis, such that the opening into the flow channel is at a transverse angle relative to the flow axis, and
  the opening having a D shape or a lens shape, viewed along the flow axis; and
an output nozzle positioned at an end of the flow channel opposite the opening so that a central axis of the output nozzle is parallel to but offset from the flow axis, such that each of the opening and the output nozzle does not completely overlap the other.

15. The mouthpiece of claim 14, wherein:
the output nozzle has a nozzle opening facing away from the opening in a direction that is normal to the flow axis; and
the nozzle opening has an ovular cross section with a cross-sectional area that is larger than a cross-sectional area of the opening configured to receive respiratory air.

16. The mouthpiece of claim 14, further comprising a flange positioned between the output nozzle and the upper and lower body portions, the flange configured to mount the mouthpiece on a device for measuring a parameter of the received respiratory air.

17. A mouthpiece for a device for measuring a parameter of respiratory air, comprising:

an upper body portion with a first end edge; and
a lower body portion with a second end edge, wherein
  the upper and lower body portions together define a flow channel along a flow axis such that the first and second end edges form an opening into the flow channel configured to receive respiratory air,
  the first end edge is positioned beyond the second end edge along the flow axis, such that the opening into the flow channel is at a transverse angle relative to the flow axis, and
  the opening has a D shape or a lens shape, viewed along the flow axis
  the upper body portion has an arcuate cross section that tapers outwards and decreases in curvature along the flow axis in a direction away from the opening; and
  the lower body portion has:
    a first section with a concave curved shape extending from the second end edge; and
    a second section extending from the first section, and tapering outwards congruous with the outward taper of the upper body portion.

18. A mouthpiece for a device for measuring a parameter of respiratory air, the mouthpiece comprising:

an upper body portion with a first end edge;
a lower body portion with a second end edge,
  the upper and lower body portions together defining a flow channel along a flow axis such that the first and second end edges form an opening into the flow channel configured to receive respiratory air, and
  the opening having a D shape or a lens shape, viewed along the flow axis; and
an outlet nozzle positioned at an end of the flow channel opposite the opening, and configured such that the respiratory air flows out of the mouthpiece via the outlet nozzle, the outlet nozzle including a lateral projection protruding radially outward from an outer surface of the outlet nozzle and extending along a direction of the flow axis, the lateral projection configured to orient the mouthpiece relative to the device when the mouthpiece is coupled to the device.

* * * * *

UNITED STATES PATENT AND TRADEMARK OFFICE
CERTIFICATE OF CORRECTION

PATENT NO. : 10,327,669 B2
APPLICATION NO. : 15/011945
DATED : June 25, 2019
INVENTOR(S) : Reisinger et al.

Page 1 of 1

It is certified that error appears in the above-identified patent and that said Letters Patent is hereby corrected as shown below:

In the Claims

1: In Column 8, Line 9, Line 1 of Claim 3 should read:
3. The mouthpiece according to claim 2, wherein:

2: In Column 8, Line 18, Line 1 of Claim 4 should read:
4. The mouthpiece according to claim 2, wherein the 3: In Column 8, Line 21, Line 1 of Claim 5 should read:
5. The mouthpiece according to claim 2, wherein the 4: In Column 8, Line 24, Line 1 of Claim 6 should read:
6. The mouthpiece according to claim 2, wherein the 5: In Column 8, Line 27, Line 1 of Claim 7 should read:
7. The mouthpiece according to claim 2, wherein the Signed and Sealed this
Seventeenth Day of September, 2019

Andrei Iancu
*Director of the United States Patent and Trademark Office*